United States Patent [19]

Hermansky

[11] Patent Number: 5,599,768

[45] Date of Patent: Feb. 4, 1997

[54] STABILIZATION OF NON-AQUEOUS SUSPENSIONS

[75] Inventor: Clarence G. Hermansky, Wilmington, Del.

[73] Assignee: E. I. du Pont de Nemours and Company, Wilmington, Del.

[21] Appl. No.: 336,602

[22] Filed: Nov. 9, 1994

Related U.S. Application Data

[63] Continuation of Ser. No. 842,200, filed as PCT/US90/05213, Sep. 19, 1990, abandoned, which is a continuation-in-part of Ser. No. 410,656, Sep. 21, 1989, abandoned.

[51] Int. Cl.⁶ ................................................. A01N 25/22
[52] U.S. Cl. .................. 504/116; 504/211; 504/234; 504/330; 71/DIG. 1; 514/63; 514/369; 514/383; 514/395; 514/772.3; 514/773; 514/777; 514/937; 514/970
[58] Field of Search .............................. 504/116, 234, 504/330, 211; 71/DIG. 1; 514/395, 63, 383, 369, 772.3, 773, 777, 937, 970

[56] References Cited

U.S. PATENT DOCUMENTS

| | | | |
|---|---|---|---|
| 3,171,779 | 3/1965 | McCoy et al. | 167/42 |
| 3,920,442 | 11/1975 | Albert et al. | 71/92 |
| 4,071,617 | 1/1978 | Graves et al. | 424/78 |
| 4,324,781 | 4/1982 | Okamoto et al. | 424/78 |
| 4,367,089 | 1/1983 | Adams, Jr. | 71/76 |
| 4,469,675 | 9/1984 | Curtis et al. | 424/78 |
| 4,664,909 | 5/1987 | Marschner | 424/65 |
| 4,678,666 | 7/1987 | Nozawa et al. | 424/81 |
| 5,074,905 | 12/1991 | Frisch et al. | 71/120 |
| 5,206,021 | 4/1993 | Dookhith et al. | 424/405 |

FOREIGN PATENT DOCUMENTS

| | | |
|---|---|---|
| 0243872 | 11/1987 | European Pat. Off. . |
| 0251464 | 1/1988 | European Pat. Off. . |
| 5-8881 | 9/1978 | Japan . |
| 60-32701 | 7/1983 | Japan . |
| 719360 | 12/1954 | United Kingdom . |
| WO90/07277 | 7/1990 | WIPO . |

OTHER PUBLICATIONS

Napper, D. H., "Polymeric Stabilization of Colloidal Dispersion", Academic Press (1983).

Tadros, Th.F. (Ed.), "The Effect of Polymers on Dispersion Properties", Academic Press (1982).

*Primary Examiner*—S. Mark Clardy

[57] ABSTRACT

A formulation consisting of an active ingredient (herbicide or pesticide) suspended in an organic medium containing, in addition to usual additives, a polymer and protic solvent and a process for the preparation of such formulation.

26 Claims, No Drawings

STABILIZATION OF NON-AQUEOUS SUSPENSIONS

This is a continuation of application Ser. No. 07/842,200, filed Mar. 19, 1992, now abandoned, from International Application No. PCT/US90/05213, filed Sep. 19, 1990, which is a continuation-in-part of application Ser. No. 07/410,656, filed Sep. 21, 1989, now abandoned.

BACKGROUND OF THE INVENTION

1. Field of the Invention

Suspensions of relatively insoluble pesticides in organic solvents are stabilized by combinations of selected polymers and protic solvents.

2. Description of Related Art

The use of polymers to stabilize aqueous suspensions is known in the art as disclosed by D. H. Napper, "Polymeric Stabilization of Colloidal Dispersions", Academic Press (1983); and Th. F. Tadros (Ed.), "The Effect of Polymers on Dispersion Properties", Academic Press (1982). However, the foregoing do not disclose or suggest the specific combination of polymer(s) and protic solvent(s) of the present invention.

SUMMARY OF THE INVENTION

Organic-based suspensions in which an active ingredient with solubility of less than one-tenth of one percent by weight in the organic medium is stabilized from settling by the addition of a water-soluble or water-swellable polymer(s) and a protic solvent(s) that structure the organic medium and thereby improve the stability and useful life of formulations. The medium may contain another soluble active ingredient(s). More particularly, a process is provided for stabilizing a suspension of one or more insoluble active ingredients from settling e.g. pesticides in an organic-based medium, the ingredients being less than 0.1% soluble in the organic-based medium, by adding to the suspension a system of at least one polymer and at least one protic solvent. The present invention also contemplates an improved formulation comprising or consisting essentially of a suspension in an organic-based medium, of one or more active ingredients, said ingredients being less than 0.1% soluble in the organic-based medium, wherein the suspension is stabilized from settling by adding to the suspension a system consisting of a mixture of at least one polymer and at least one protic solvent.

One embodiment is a suspension having at least one ingredient in the ranges indicated (percentages are by weight based on total formulation weight and preferred ranges are in parenthesis):

0.1–50% (10–50%) substantially insoluble active ingredient(s) (<0.1% solubility in the medium)

20–99% (20–60%) organic medium 0.01–5% (0.1–2%) suspending agents and sufficient emulsifier for good suspension of the final product in water, and in addition a system of both of the following:
0.1–15% (0.5–10%) polymer(s)
0.5–20% (0.5–15%) protic solvent(s).

In a preferred embodiment the polymer(s) are water-swellable and especially water-soluble; the active ingredient is at least one pesticide or a chemical used for crop protection, more specifically, ingredients are selected from the class of herbicides, fungicides, bactericides, insecticides, insect antifeedants, acaricides, miticides, nematocides, and plant growth regulants, and the organic medium is selected from oxygenated and nonoxygenated solvents from the class of petroleum solvents; aromatic and non-aromatic hydrocarbons; halogenated aromatic and non-aromatic hydrocarbons; aromatic and non-aromatic ethers, esters, amides, ketones; alcohols; Cellosolves; and oils including but not limited to vegetable oils or paraffin oils.

In an especially preferred embodiment the ingredients are as above mentioned and, in addition, the suspending agents are hydrophilic and hydrophobic silicas, colloidal silicon dioxides, montmorillonite, organically modified montmorillonite clays; the polymers are synthetic and naturally occurring polymers, biopolymers, selected from the class consisting of, but not limited to:

Polyvinyl Ethers

Polyvinyl Pyrrolidones

Polypropylene oxide-polyethylene oxide condensates

Polyvinyl Acetates

Maleic Anhydrides

Polypropylene Glycols

Modified Polyacrylic Acids

Polyacrylonitrile Block Copolymers

Polysaccharides

Proteins

Carbohydrates and the protic solvents are selected from the class of polar, substantially water-soluble molecules with one or more hydrogen atoms that exchange rapidly under weakly basic, neutral or acidic conditions, such as the hydrogen atoms found on the heteroatoms of functional groups including, but not limited to alcohols, thiols, imides, ammonium salts, and carboxylic acids or mixtures thereof.

Preferred active ingredients are selected from the class consisting of, but not limited to: benzimidazoles, triaznies and sulfonylureas.

DETAILED DESCRIPTION OF THE INVENTION

A common method for stabilizing a suspension of one or more active ingredients in an organic-based medium is to use thickeners and/or suspending agents to increase the viscosity of the medium in which they are suspended. This invention incorporates a combination of at least one polymer(s) and at least one protic solvent(s) in addition to the known suspension systems to create physically stable suspensions.

The stabilized suspensions of this invention do not compromise performance. The instant suspension concentrates are pourable, disperse into water using minimal or no agitation. The aqueous dispersions obtained by addition of the concentrates to water can be sprayed through conventional spray nozzles in which 50 mesh screens precede each nozzle to protect it from blockage. The dispersions have little tendency to form films in water, which films can also plug nozzle screens.

The suspensions detailed in this invention are obtained by the combination of the insoluble active ingredient(s) (as above defined) with other inert ingredients: organic medium, suspending agents, emulsifier and/or dispersant, polymer(s) and protic solvent(s); additional soluble active ingredients may also be present. For example, pesticides and crop protection chemicals, including herbicides, fungicides, bactericides, insecticides, insect antifeedants, acaricides, miticides, nematocides and plant growth regulants.

By organic medium is meant a substantially water-insoluble organic liquid(s) in which the particles are to be suspended which is essentially inert towards the active ingredient and other additives. Especially useful media singly or in combination include aromatic and non-aromatic hydrocarbons; halogenated aromatic and non-aromatic hydrocarbons; aromatic and non-aromatic ethers, esters or amides; and oils including but not limited to vegetable oils or paraffin oils. Additionally, the medium can include any of the above in which other active ingredient(s) have been solubilized.

Also known in the art is the selection of an emulsifier, which can also serve to function as a wetting agent and dispersant because of the similar surface activity possessed by all three of these additives. However, just as important as wetting and dispersion in organic-based suspension concentrates is the ability to insure that the medium will emulsify when added to water,land that the emulsion will not break for a period which is long enough for the intended application. Often non-ionic/anionic surfactant blends are used as emulsifiers. Their selection is primarily governed by the medium of interest. The theory and practical methods of selecting emulsifiers are given in great detail in the open literature. See for example P. Becher, "Emulsions: Theory and Practice", 2nd Ed., New York, Reinhold (1965).

Suspending agents are traditionally added to reduce the settling rate of the particles in the suspension. These materials usually increase the viscosity of the medium. Solid particles, namely clays and oxides, which are finer than those of the active ingredient(s) are also used to retard settling in both aqueous and non-aqueous media. These solids may form three-dimensional networks (gels) in the medium and thereby retard the Settling of the coarser active ingredient(s). Naturally occurring and synthetic macromolecules such as gums, starches, cellulose and polymers are also used alone and in combination with clays and oxides. Although it known that the combination of these ingredients often results in better suspensions than those produced by either component alone, this is known to be effective only in aqueous systems. Specifically, the use of polymers, such as those described in this invention, has been restricted to aqueous systems, and their mode of action is always attributed either to a simple increase in viscosity or to "steric stabilization". The latter usually involves adsorption of the polymer to the particle surface to form a steric barrier, or stabilization, which results from osmotic force that develop when the polymer concentration is depleted between particles as they approach one another.

Methods for preparing dispersions of particles in a liquid are well known in the art. See, for example, G. D. Parfitt, "Dispersion of Powders in Liquids", Applied Science Pub. Ltd. (1973); and Th. F. Tadros, "Advances in Colloid and Interface Science", 12 (1980). In general, the insoluble active ingredient(s) is usually added to the medium as a micronized powder of less than 10 microns in size, on average, or as a coarser solid which is then reduced in size to below 10 microns, on average, by a wet milling process. In the former case, the formulation need only be stirred in order to disperse the solids, unless the micronized powder is present in aggregates in which the primary particles are held together by forces strong enough to make stirring impractical. In this case, wet milling is also required to break up the aggregates and reduce the solids down to the primary particle size.

The purpose of the dispersion process is to allow the medium to "wet" the surface of the particles and to displace the air between particles. The efficiency of the wetting process can be greatly improved by the addition of wetting agent(s), to reduce the work required to wet the particle surface. A dispersant(s) may also be required to serve the function of keeping the particles separated once they have been dispersed. Dispersants are also used to keep the particles separated further dilution by the medium or on addition of the suspension concentration to water or a spray oil. The use and selection of dispersants and wetting agents are well known in the art. See T. C. Patton, "Paint Flow and Pigment Dispersion", Wiley (1979).

In this invention, the traditional methods just described are replaced or enhanced by the heretofore unknown synergistic effect of the combination of water-soluble or water-swellable polymer(s) and protic solvent(s) in an organic medium.

Polymers which are used in the present invention include those water-soluble or water-swellable organic macromolecules with weight average molecular weights from 1,000 to several million. Examples include, but are not limited to, polyvinyl methyl ether, polyvinyl pyrrolidone, polypropylene glycol, polyethylene glycol-polypropylene glycol condensates, polyvinyl alcohol, polyvinyl acetate, polyvinyl alcohol/polyvinyl acetate copolymers, polyacrylic acid, and styrene maleic anhydride. The important characteristics of the polymer(s) are surface activity and measurable, but not excessive, solubility of the polymer(s) in both water and the organic medium. Finally, the polymer must be selected such that it has a maximal stabilizing effect on the suspension, as described below.

Specifically preferred are the polyethylene glycol-polypropylene glycol condensates such as the Pluronic® series, the polyvinyl pyrrolidones such as PVP-K® series and the modified polyacrylic acids such as polyacrylamide Cyanamer® series.

Protic solvents operable in the present invention include polar, substantially water-soluble liquids with one or more hydrogen atoms that exchange rapidly under weakly basic, neutral or acidic conditions, such as the hydrogen atoms found on the heteroatoms of functional groups including, but not limited to, alcohols, thiols, imides, ammonium salts and carboxylic acids. The hydrogen atoms must also form hydrogen bonds with hydrogen bond accepting atoms such as oxygen, nitrogen or halogen. These effects are described in detail in J. March, "Advanced Organic Chemistry", 3d Ed., pp. 71–74, Wiley, N.Y., (1985).

Preferred solvents are water and propylene glycol.

Addition of the polymer(s) and protic solvent(s) at any step in the formulating process is acceptable, provided the polymer(s) does not degrade during wet milling. If stability to wet milling is not known, the effect of mechanical energy on the polymer(s) in question can be determined by comparing the properties of a formulation made by post-milling addition of the polymer(s) and protic solvent to the properties which result when these ingredients are added before mechanical energy is applied.

By adjusting the amount and ratio of polymer(s) and protic solvent(s), the resultant hard-packed, difficult-to-resuspend sediment that accompanies the more traditional methods of stabilizing particles suspended in non-aqueous media is eliminated without compromising the desirable handling characteristics of the suspension concentrate, i.e. pourability, pumpability and attractive visual appearance.

The optimum effect described above can be monitored by the combination of visual observation and experimental measurement. Traditionally, the stability of suspension concentrates has been related to the viscosity of the suspension at low shear rates and its yield point or yield value. In the examples of this invention, viscosity was measured using a rotational viscometer. Rotational viscometers are standard instruments, readily available from companies such as Haake, Contraves, Carri-Med, and Brookfield. Both the instrument and accompanying geometry (parallel plate, cone and plate, concentric cylinder sample compartments) can be used to accurately measure viscosity by applying a fixed angular velocity to the sample by rotating one of the geometric members. Then, using accurate measurements of the stress developed on the "stationary" geometric member, the viscosity is given by the ratio of the stress to the applied shear rate. Geometric constants, equations and instrumentation to automate this calculation are routinely supplied along with these instruments.

The above determination can be run over a range of shear rates to give a series of viscosities which correspond to the applied shear rates. Thereafter, the Bingham Equation can be applied to the data to calculate the yield stress or yield point of the sample. This is done by plotting the stress vs. shear rate and extrapolating the data to a shear rate of zero. The intercept of the plot is the yield stress. A more in-depth review of the art can be found in many texts on viscometry, rheology or rheometry. The following references contain such information: 1) K. Walters, "Rheometry: Industrial Applications", Research Studies Press (1980), 2) P. Sherman, "Industrial Rheology", Academic Press (1970), 3) T. C. Patton, "Paint Flow and Pigment Dispersion", Wiley (1979). If the viscosity at low shear rates and/or the yield value of the suspension is high enough, settling of the particles in suspension can be retarded and even prevented within the commercial time frame of interest. With traditional methods, achieving this effect often compromises preferred properties such as visual acceptability and the ability to pour and pump the suspension. Polymer(s)/protic solvent(s) stabilization is an advance over the art in that it provides a means by which the viscosity and yield values can be increased to a level which will stabilize the suspension against settling and enhance the visual appearance of the suspension, without negatively impacting the ease with which it can be poured or pumped. In fact, one of the indicators that a polymer/protic solvent pair has effectively increased the viscosity and yield value of a suspension is a change in consistency relative to a control or reference sample. Typically, within 1–3 days after preparation, the suspension's consistency has appreciably increased over that of the control, and it usually follows that the viscosity and yield values have also increased significantly. Conversely, if the consistency is the same as the control or in any way visually unacceptable, or an appreciable separation of phases has occurred, either the polymer/protic solvent pair is not a good match to the suspension of interest or the level and/or ratio of the polymer and protic solvent requires adjustment.

Thus, the correct combination of ingredients can be determined by one skilled in the art as follows, wherein the correct combination is compared to a reference sample, which reference sample contains medium in place of both polymer and protic solvent;

a) the ingredients are selected by visual inspection, in which the beneficial effect of the invention is demonstrated by an increase in consistency ("body") and ability to resist flow on tilting, usually within 24 hours of preparation, or b) the ingredients are selected by viscosity measurement in which the beneficial effect of the invention is demonstrated by an increase in viscosity of at least twenty percent, or c) the ingredients are selected by yield stress measurement, in which the beneficial effect of the invention on the suspension is demonstrated by an increase in yield point of at least twenty percent, or d) the ingredients are selected as in a) and b) such that both viscosity and yield point are increased by a minimum of ten percent.

The following examples are presented to illustrate but not to restrict the present invention. Parts and percentages are by weight based upon the total weight of the formulation unless otherwise noted.

All of the ingredients listed, with the exception of the polymer and protic solvent, were passed once through a 0.6 liter Dyno Mill (Type KDL) operating at a flow rate of 100 ml./min. The resulting particulate weight average diameters were between 2 and 10 microns. The polymer and protic solvent were added after the milling step, and the resulting formulation was evaluated after a 1 to 3 day equilibration period. Unless otherwise stated, the control or reference sample to which comparisons were made contained medium in place of polymer or protic solvent, to insure that the active and formulating ingredient levels would remain constant.

EXAMPLES 1 TO 10

Examples 1 to 3 illustrate the stabilizing effect of polyvinyl methyl ether (PVME) and water in an aromatic medium base in which a second active ingredient, flusilazol, has been dissolved.

| INGREDIENT | PERCENT |
| --- | --- |
| Flusilazol | 24.3 |
| Carbendazim (MBC) | 12.1 |
| Atlox ® 3453F | 30.0 |
| Halso ® 99 | 8.6 |
| Bentone ® 38 | 0.5 |
| Aerosil ® 200 | 2.0 |
| Xylenes | 22.5 |
| Polyvinyl Methyl Ether (PVME) | (a) |
| Water | (a) |

The exact composition of the sample is given by reducing the medium (Halso 99 and Xylenes) proportionately to compensate for the addition of water and polymer.

TABLE I

| EXAMPLE | POLYMER | WATER | VISCOSITY (Poise) 0.002 $S^{-1}$ | VISCOSITY (Poise) 0.008 $S^{-1}$ | YIELD POINT (dynes/cm$^2$) |
| --- | --- | --- | --- | --- | --- |
| 1 | PVME 0.75% | 1.0% | — | — | 3.7 |
| 2 | PVME 1.0% | 1.0% | 1620 | 450 | |
| 3 | PVME 2.5% | 2.5% | — | — | 6.0 |
| CONTROL | NONE | NONE | 70 | 22 | 3.7 |
| CONTROL | NONE | 1.0 | 19.5 | 6.5 | 0.6 |
| CONTROL | PVP ® K-30 4.8% | NONE | 6.6 | 1.8 | 0.5 |
| CONTROL | SMA ® 3000 4.8% | NONE | 30.3 | — | 0.3 |
| CONTROL | PPG-4025 10% | NONE | 25.7 | 14.6 | 0.9 |
| 4 | PVP ® K30 1.0% | 1.0% | 266 | 71 | 7.1 |
| 5 | PEO-PPO | 1.0% | 109 | 30 | 4.1 |

TABLE I-continued

| EXAMPLE | POLYMER | WATER | VISCOSITY (Poise) 0.002 $S^{-1}$ | VISCOSITY (Poise) 0.008 $S^{-1}$ | YIELD POINT (dynes/ $cm^2$) |
|---|---|---|---|---|---|
| | COPOLYMER PLURONIC® P104 1.0% | | | | |
| 6 | PEO-PPO COPOLYMER PLURONIC® L61 1.0% | 1.0% | 170 | 52 | 8.1 |
| 7 | PVA VINOL® 107 1.0% | 1.0% | 113 | 25 | 4.5 |
| 8 | SMA® 3000 1.0% | 1.0% | 101 | 32 | 5.4 |
| 9 | PPG-4025 1.0% | 1.0% | 100 | 37 | 7.2 |
| 10 | PAA CYANAMER® A A-370 1.0% | 1.0% | 66 | 20 | 2.9 |

There were two control samples for Examples 1, 2 and 3. One did not contain polymer and the other did not contain polymer or protic solvent. Both control samples had the consistency of water. The consistency of Examples 2 and 3 was significantly increased over that of the control samples, having more "body" and ability to resist flow on tilting. However, the consistency of Example 1 was not different from the control samples illustrating the need for adequate levels of both polymer and protic solvent for the invention to work. Examples 4 through 10 further exemplify the breadth of polymers which are effective in structuring non-aqueous suspensions when combined with a protic solvent. The increased consistency, viscosity and yield point of Examples 1–10 result in a formulation that settles much more slowly than the water-thin controls, thus providing better shelf-life and appearance.

EXAMPLES 11 AND 12

Examples 11 and 12 illustrate the invention s applicability to Hexythiazox (Miticide) particulates, suspended in a soybean n-butyl acetate based medium. Pluronic® L61 and water were used to stabilize the suspension.

| | (Percent) | |
|---|---|---|
| Ingredients | Example 11 | Example 12 |
| Flusilazol | 24.3 | 24.7 |
| Hexythiazox Technical | 20.0 | 18.0 |
| Soybean Oil | 27.0 | 24.7 |
| n-butyl Acetate | 13.6 | 12.4 |
| Flomo® 2X | 4.5 | 4.1 |
| Aerosil® 927 | 0.18 | 0.16 |
| Aerosil® 200 | 0.35 | 0.32 |
| Pluronic® L61 | 6.0 | 12.0 |
| Water | 4.0 | 8.0 |

The control (no polymer or water) had the consistency of water, whereas, the consistency, body and ability to resist flow on tilting of Examples 11 and 12 showed significant increases over the control (no Pluronic® L61 or water). The viscosity and yield points for these systems are given in the following table. The increase consistency, viscosity and yield point of Examples 1–10 result in a formulation that settles much more slowly than the water-thin controls, thus providing better shelf-life and appearance.

TABLE II

| EXAMPLE | POLYMER | WATER | VISCOSITY (Poise) 0.02 $S^{-1}$ | VISCOSITY (Poise) 0.08 $S^{-1}$ | YIELD POINT (dynes/ $cm^2$) |
|---|---|---|---|---|---|
| CONTROL | NONE | NONE | 2.5 | 1.0 | 0.04 |
| 11 | PEO-PPO COPOLYMER PLURONIC® L61 6.0% | 4.0% | 6.2 | 1.4 | 0.9 |
| 12 | PEO-PPO COPOLYMER PLURONIC® L61 12.0% | 8.0% | 228 | 60 | 5 |

EXAMPLES 13 TO 19

Examples 13 to 19 illustrate the applicability of the invention to atrazine herbicide particulates suspended in a medium based on soybean oil and n-butyl acetate. Pluronic® L61 and one or more of the following protic solvents were used: water, propylene glycol, sorbitol, n-butanol, diethylene glycol.

| Ingredients | (Percent) |
|---|---|
| Flusilazol | 26.2 |
| Atrazine Technical | 11.3 |
| Soybean Oil | 29.2 |
| n-butyl Acetate | 14.7 |
| Flomo® 2X | 4.9 |
| Aerosil® 927 | 0.19 |
| Aerosil® 200 | 0.38 |

| | EXAMPLES | | | | | | |
|---|---|---|---|---|---|---|---|
| | 13 | 14 | 15 | 16 | 17 | 18 | 19 |
| Pluronic® L61 | 8.7 | 4.3 | 8.7 | 8.7 | 8.7 | 8.7 | 8.7 |
| Propylene Glycol | | 4.3 | | 4.3 | | | |
| Sorbitol | | | 2.2 | | 4.3 | | |
| n-butanol | | | | | | 4.3 | |
| Diethylene Glycol | | | | | | | 4.3 |
| Water | 4.3 | 4.3 | 2.1 | | | | | a. Examples 13 to 19 contained a fixed percentage of all ingredients except the polymer and aprotic solvent(s) listed above.

The control (no polymer or protic solvent) had the consistency of water, whereas the consistency of all of the samples represented by Examples 13 to 19 were significantly increased by the addition of the polymer and protic solvent(s). Examples 13 to 19 had more "body" and ability to resist flow on tilting than did the control. To quantify the effect, the viscosity and yield points of Examples 13 to 15 are given in the following table. The increased consistency, viscosity and yield point of Examples 1–10 result in a formulation that settles much more slowly than the water-thin controls, thus providing better shelf-life and appearance.

TABLE III

| EX-AMPLE | POLYMER | WATER | VISCOSITY (Poise) 0.002 S$^{-1}$ | VISCOSITY (Poise) 0.008 S$^{-1}$ | YIELD POINT (dynes/cm$^2$) |
|---|---|---|---|---|---|
| CONTROL | NONE | NONE | 487 | 150 | 1 |
| 13 | PEO-PPO COPOLYMER PLURONIC® L61 8.7% | 4.3 | >1200 | 850 | 3.0 |
| 14 | PEO-PPO COPOLYMER PLURONIC® L61 4.3% | 4.3 | >2000 | 1100 | 2.0 |
| 15 | PEO-PPO COPOLYMER PLURONIC® L61 8.7% | 2.1 | >1000 | 400 | 4.0 |

EXAMPLES 20 TO 21

Examples 20 to 21 illustrate the applicability of the invention to diuron herbicide particulates, suspended in a medium based on soybean oil and n-butyl acetate. Pluronic® L61, water and a water/propylene glycol blend were used to stabilize the particulates in the following examples.

| Ingredients | (Percent) Example 20 | (Percent) Example 21 |
|---|---|---|
| Flusilazol | 23.2 | 23.2 |
| Diuron Technical | 10.1 | 10.1 |
| Soybean Oil | 25.8 | 25.8 |
| n-butyl Acetate | 13.0 | 13.0 |
| Flomo® 2X | 4.3 | 4.3 |
| Aerosil® 927 | 0.2 | 0.2 |
| Aerosil® 200 | 0.4 | 0.4 |
| Pluronic® L61 | 19.2 | 19.2 |
| Propylene Glycol | 0.0 | 1.9 |
| Water | 3.9 | 1.9 |

The control(no polymer or protic solvent) was thin, having the consistency of water. The consistency of the compositions given by Examples 20 and 21 were increased significantly by the polymer/solvent system, relative to the control. Both had more "body" and ability to resist flow on tilting than did the control. The viscosity and yield points of Examples 20 and 21 are given in the following table. The increased consistency, viscosity and yield point of Examples 1–10 result in a formulation that settles much more slowly than the water-thin controls, thus providing better shelf-life and appearance.

TABLE IV

| EX-AMPLE | POLYMER | PROTIC SOLVENT | VISCOSITY (Poise) 0.002 S$^{-1}$ | VISCOSITY (Poise) 0.008 S$^{-1}$ | YIELD POINT (dynes/cm$^2$) |
|---|---|---|---|---|---|
| CONTROL | NONE | NONE | <1.7 | 1.8 | <0.01 |
| 20 | PEO-PPO COPOLYMER PLURONIC® L61 19.2% | WATER 3.9% | 200 | 30 | 1 |
| 21 | PEO-PPO COPOLYMER PLURONIC® L61 19.2% | WATER 1.9% PROPYLENE GLYCOL 1.9% | 300 | 40 | 2 |

EXAMPLES 22 TO 24

Examples 22 to 24 illustrate the applicability of the invention to carbendazim fungicide particulates, suspended in an aliphatic hydrocarbon based medium. The stabilizing polymer used was 2-polyvinyl pyrrolidone (PVP® K-30), and protic solvents were water, glycerol, or dipropylene glycol.

| Ingredients | (Percent) Example 22 | (Percent) Example 23 | (Percent) Example 24 |
|---|---|---|---|
| Orchex | 30.9 | 30.9 | 37.5 |
| Carbendazim Technical | 20.6 | 20.6 | 25.0 |
| Atplus 300F | 15.4 | 15.4 | 18.8 |
| PVP® K-30 | 10.3 | 10.3 | 12.5 |
| Water | 12.5 | | |
| Glycerol | | 12.5 | |
| Dipropylene Glycol | | | 6.2 |

The control was thin. The control contained 10.3% PVP® K-30, but did not contain a protic solvent. The consistency of the compositions given by Examples 22 to 24 was increased significantly by the use of protic solvent and polymer Examples 22 to 24 had more "body" and ability to resist flow on tilting than the control. The increased consistency, viscosity and yield point of Examples 1–10 result in a formulation that settles much more slowly than the water-thin controls, thus providing better shelf-life and appearance. The viscosity and yield points of Examples 22 to 24 are given in the following table.

TABLE V

| EX-AMPLE | POLYMER | PROTIC SOLVENT | VISCOSITY (Poise) 0.002 S$^{-1}$ | VISCOSITY (Poise) 0.008 S$^{-1}$ | YIELD POINT (dynes/cm$^2$) |
|---|---|---|---|---|---|
| CONTROL | NONE | NONE | 1593 | 850 | 26.2 |
| 22 | PVP® K-30 10.3% | WATER 12.5% | 3450 | 1500 | 39.4 |
| 23 | PVP® K-30 10.3% | GLYCEROL 12.5% | 1880 | — | — |
| 24 | PVP® K-30 12.5% | DIPROPYLENE GLYCOL 6.2% | 1820 | | |

EXAMPLES 25 TO 26

Examples 25 and 26 illustrate the invention s applicability to nicosulfuron (sulfonylurea) particulates, suspended in a corn oil based medium. Polyvinyl methyl ether (PVME) and water were used to stabilize the suspension.

| Ingredients | (Percent) |
|---|---|
| Corn Oil | 76.2 |
| Atlox ® 848D | 15.6 |
| Bentone ® SD-1 | 3.1 |
| V9360 Sulfonyl Urea | 4.5 |
| Aerosil ® 200 | 0.6 |
| PVME | (a.) |
| Water | (a.) | a. The exact composition of the sample is given by a one-to-one replacement, by weight, of the corn oil with the polymer and protic solvent of interest.

Two controls were run. Both had t he consistency of water, whereas, the consistency, body and ability to resist flow on tilting of Examples 25 and 26 showed significant increases over the controls. To quantify the effect, the viscosity and yield points of Examples 25 and 26 are given in the following table. The increased viscosity and yield point of the examples, relative to the controls, result in formulations which settle much more slowly than the controls, thus providing better shelf-life and appearance.

TABLE VI

| EXAM- | | | VISCOSITY (Poise) | | YIELD POINT |
|---|---|---|---|---|---|
| PLE | PVME | WATER | $0.002\ S^{-1}$ | $0.008\ S^{-1}$ | (dynes/cm$^2$) |
| Control | None | None | 3.7 | 1.1 | ~0 |
| Control | None | 5.7% | 75 | 45 | 93 |
| 25 | 5.7% | 5.7% | 317 | 146 | 192 |
| 26 | 5.7% | 10.3% | 453 | 227 | 331 |

EXAMPLES 27 TO 30

In Examples 27 to 30, Kelzan® and Kelset® polysaccharides and Aqualon® HP-007 cross-linked polysaccharide (gums) were used in combination with water and propylene glycol (protic solvents) to illustrate the use of biopolymers in this invention. The active ingredients were Carbendazim (MBC) particulates and Flusilazol. The latter is soluble in the medium, which consists of a mixture of Halso® 99 and xylenes.

| Ingredients | (Percent) |
|---|---|
| Flusilazol | 24.3 |
| Carbendazim (MBC) | 12.1 |
| Atlox ® 3453F | 30.0 |
| Halso ® 99 | 8.6 |
| Bentone ® 38 | 1.1 |
| Aerosil ® 200 | 2.4 |
| Xylene | 21.0 |
| Polymer | (a) |
| Propylene Glycol | (a) |
| Water | (a) |

The exact composition of the sample is given by reducing all of the above ingredients proportionately to compensate for the addition of polymer and protic solvent.

TABLE VII

| EX-AMPLE | POLYMER | PROTIC SOLVENT | VISCOSITY (Poise) | | YIELD POINT |
|---|---|---|---|---|---|
| | | | $0.002\ S^{-1}$ | $0.009\ S^{-1}$ | (dynes/cm$^2$) |
| Control | None | None | 80 | 20 | |
| Control | None | Water 1.7% | 864 | 272 | |
| Control | Kelzan ® 0.5% | None | 65 | 48 | |
| 27 | Kelzan ® 0.5% | Water 1.7% | 1570 | 618 | |
| Control | None | Propylene Glycol 2.9% | 38 | 31 | 2.6 |
| 28 | Kelset ® 0.5% | Propylene Glycol 2.9% | 58 | 42 | 4.3 |
| 29 | Kelzan ® 0.5% | Propylene Glycol 2.9% | 45 | 34 | 5.0 |
| 30 | Aqualon ® HP-007 0.5% | Propylene Glycol 2.9% | 51 | 41 | 4.5 |

What is claimed is:

1. A process for stabilizing a suspension, said suspension consisting of in weight percent based on total formulation weight, 0.1–50% of at least one active ingredient;

20–99% organic medium; 0.01–5% of at least one suspending agent wherein the active ingredient is substantially insoluble in the organic medium, and sufficient emulsifier for suspension of the final product in water, which process comprises:

adding to the suspension 0.1–15% of at least one of a water-swellable or water-soluble polymer selected from the class consisting of:

polyvinyl ethers, polyvinyl pyrrolidones, polypropylene oxide-polyethylene oxide condensates, polyvinyl acetates, maleic anhydrides, polypropylene glycols, modified polyacrylic acids, polyacrylonitrile block copolymers, polysaccharides, polysaccharide derivatives, proteins, carbohydrates, and mixtures of the foregoing; and 0.5–15% of at least one protic solvent.

2. The process of claim 1 wherein the polymer is a member selected from the class consisting of:

Polyvinyl methyl ether (PVME, M.W. 1–5,000)

Polyvinyl pyrrolidone, (PVP M.W. ~25–100,000)

Polypropylene oxide-polyethylene oxide condensates (PPO-PEO, M.W. 1–10,000)

Polyvinyl acetate (PVA, M.W. 5–50,000)

Styrene maleic anhydride (SMA, 1–10,000)

Polypropylene glycol (PPG, 1–10,000)

Modified polyacrylic acid (PAA, 1–500,000)

Xanthan Gum

Algenates

Cellulose Derivatives and mixtures of the foregoing.

3. The process of claim 2 wherein the polymer is a member selected from, the class consisting of:

Polyvinyl methyl ether (PVME, M.W. 2–3,000)

Polyvinyl pyrrolidone (PVP M.W. ~40,000)

Polypropylene oxide-polyethylene oxide condensates (PPO-PEO, M.W. 2,000)

Polyproplyene oxide-polyethylene oxide condensates (PPO-PEO, M.W. 5,850)

Polyvinyl acetate (PVA, M.W. 11–31,000)

Styrene maleic anhydride (SMA, 1,000)

Polypropylene glycol (PPG, 4,000)

Modified polyacrylic acid (PAA, 200,000) and mixtures of the foregoing.

4. The process of claim 1 wherein the suspension consists of in weight percent based on total formulation weight, 10–50% active ingredient, 20–60% organic medium and 0.1–2% suspending agent and 0.5–10% polymer and 0.5–15% protic solvent are added to the suspension.

5. The process of claim 4 wherein the organic medium is a member selected from the class consisting of oxygenated and nonoxygenated solvents from the class of petroleum solvents; aromatic and non-aromatic hydrocarbons; halogenated aromatic and non-aromatic hydrocarbons; aromatic and non-aromatic ethers, esters, amides, ketones; alcohols; vegetable oils; paraffin oils; and mixtures of the foregoing.

6. The process of claim 5 wherein the organic medium is a member selected from the class consisting of xylenes, chlorotoluenes, alkyl benzenes, alkyl napthalenes, aliphatic acetates, soybean oil, corn oil, cottonseed oil, paraffinic solvents and oils, and mixtures of the foregoing.

7. The process of claim 4 wherein the protic solvents are a member selected from the class consisting of water, gycerol, propylene glycol, n-butanol, n-hexanol, sorbitol, dipropylene glycol and mixtures of the foregoing.

8. The process of claim 7 wherein the polymer is water-soluble or water-swellable and is a member selected from the class of synthetic and naturally occurring polymers, biopolymers consisting of:

Polyvinyl Ethers

Polyvinyl Pyrrolidones

Polypropylene oxide-polyethylene oxide condensates

Polyvinyl Acetates

Maleic Anhydrides

Polypropylene Glycols

Modified Polyacrylic Acids

Polyacrylonitrile Block Copolymers

Polysaccharides

Polysaccharide Derivatives

Proteins

Carbohydrates

Xanthan Gum

Algenates

Cellulose Derivatives and mixtures of the foregoing.

9. The process of claim 8 wherein the polymer is a member selected from the class of synthetic, add naturally occurring polymers, biopolymers consisting of:

Polyvinyl methyl ether (PVME, M.W. 1–5,000)

Polyvinyl pyrrolidone (PMP M.W. ~25–100,000)

Polypropylene oxide-polyethylene oxide condensates (PPO-PEO, M.W. 1–10,000)

Polyvinyl acetate (PVA, M.W. 5–50,000)

Sytrene maleic anhydride (SMA, 1–10,000)

Polypropylene glycol (PPG, 1–10,000)

Modified polyacrylic acid (PAA, 1–500,000) and mixtures of the foregoing.

10. The process of claim 9 wherein the polymer is a member selected from the class consisting of:

Polyvinyl methyl ether (PVME, M.W. 2–3,000)

Polyvinyl pyrrolidone (PMP M.W. ~40,000)

Polypropylene oxide-polyethylene oxide condensates (PPO-PEO, M.W. 2,000)

Polypropylene oxide-polyethylene oxide condensates (PPO-PEO, M.W. 5,850)

Polyvinyl acetate (PVA, M.W. 11–31,000)

Styrene maleic anhydride (SMA, 1,000)

Polypropylene glycol (PPG, 4,000)

Modified polyacrylic acid (PAA, 200,000) and mixtures of the foregoing.

11. The process of claim 10 wherein the protic solvent is propylene glycol.

12. The process of claim 10 wherein the protic solvent is water.

13. The process of claim 4 wherein the active ingredient is a member selected from the class consisting of pesticides, herbicides, fungicides, bactericides, insecticides, insect antifeedants, acaricides, miticides, nematocides, plant growth regulants and mixtures of the foregoing.

14. The process of claim 13 wherein the active ingredient is hexythiazox.

15. The process of claim 13 wherein the active ingredient is a benzimidazole or mixture thereof.

16. The process of claim 15 wherein the active ingredient is carbendazim.

17. The process of claim 13 wherein the active ingredient is a triazine or mixture thereof.

18. The process of claim 17 wherein the active ingredient is atrazine.

19. The process of claim 13 wherein the active ingredient is atrazine with diuron.

20. The process of claim 13 wherein the active ingredient is a sulfonylurea.

21. The process of claim 20 wherein the active ingredient is

N-[[(4,6-dimethoxy-2-pyrimidinyl)amino]-carbonyl]-3-(ethylsulfonyl)-2-pyridine sulfonamide.

22. The process of claim 20 wherein the active ingredient is methyl 3-[[[[(4-methoxy-6-methyl-1,3,5-triazin-2-yl)amino]-carbonyl]amino]-sulfonyl]-2-thiophene-carbonate.

23. The process of claim 20 wherein the active ingredient is methyl 2-[[[[N-(4-methoxy-6-methyl-1,3,5-triazin-2-yl)-N-methylamino]carbonyl]amino]sulfonyl]benzoate.

24. The process of claim 20 wherein the active ingredient is methyl 2-[[[[[(4,6-dimethoxy-2-pyrimidinyl)amino]carbonyl]amino]-sulfonyl]methyl]benzoate.

25. The process of claim 20 wherein the active ingredient is

2-[[[[(4,6-dimethoxy-2-pyrimidinyl)amino]carbonyl]amino]sulfonyl]-N,N-dimethyl-3-pyridinecarboxamide.

26. The process of claim 20 wherein the active ingredient is methyl 2-[[[[[4,6-bis(difluoromethoxy)-2-pyrimidinyl]amino]carbonyl]amino]sulfonyl]benzoate.

* * * * *